United States Patent [19]

Burkinshaw et al.

[11] Patent Number: 5,490,853
[45] Date of Patent: Feb. 13, 1996

[54] ORTHOPEDIC BONE PLUG CUTTER

[75] Inventors: Brian D. Burkinshaw, Pflugerville; John L. Wheeler, Victoria, both of Tex.

[73] Assignee: Intermedics Orthopedics, Inc., Angleton, Tex.

[21] Appl. No.: 255,382

[22] Filed: Jun. 8, 1994

[51] Int. Cl.⁶ .................................................. A61B 17/16
[52] U.S. Cl. ................ 606/79; 606/95; 30/229; 30/130
[58] Field of Search ................ 606/79, 84, 85, 606/95; 30/229, 363, 130

[56] References Cited

U.S. PATENT DOCUMENTS

| | | | |
|---|---|---|---|
| 2,150,046 | 3/1939 | Bard | 30/130 |
| 4,817,287 | 4/1989 | Arnold et al. | 30/363 |
| 4,843,716 | 7/1989 | Lutzker | 30/130 |
| 5,071,438 | 12/1991 | Jones et al. | 623/20 |
| 5,342,364 | 8/1994 | Mikhail | 606/79 |

*Primary Examiner*—Stephen C. Pellegrino
*Assistant Examiner*—Scott B. Markow
*Attorney, Agent, or Firm*—John R. Merkling

[57] ABSTRACT

An orthopedic bone plug cutter for cutting a customized bone plug for use with prosthesis having stems of complex geometry, such as a cruciate stem. The bone plug cutter comprises an anvil which supports a piece of bone obtained intraoperatively. A specialized cutting head is forced against the anvil by a parallel jaw clamp. The cutting head can then be removed from the clamp and the bone plug extruded from the cutter with a plunger.

9 Claims, 3 Drawing Sheets

ORTHOPEDIC BONE PLUG CUTTER

FIELD OF OUR INVENTION

Our invention relates to orthopedic surgical instruments, and particularly to an instrument for cutting a specially shaped bone plug for use in connection with implanted orthopedic prostheses.

BACKGROUND OF OUR INVENTION

Orthopedic prostheses are commonly used to replaced diseased joints in the human body. Prostheses are used for such joints as the hip, the knee, the shoulder, and finger joints, among others. As a representative example, a knee prosthesis may have a femoral component which replaces the condyles of the distal femur and a tibia component which replaces the condyle compartments of the proximal tibia. Either the femoral prosthesis, or the tibial prosthesis or both may have a medullar shaft or shank which extends into the medullar canal of the femur or tibia respectively and serves to stabilize the prosthesis on the bone. Conventionally, the end of the bone is resected or shaped and a cavity is formed in the medullar canal of the bone to receive the shaft. The shaft of the prosthesis may be stabilized by the use of polymethyl methacrylate (PMMA) bone cement inserted into the prepared cavity. To prevent the PMMA cement from migrating down the cavity, surgeons have frequently prepared a customized plug of the patient's bone, formed by chipping, sawing or otherwise forming a piece of the bone salvaged during the operation. This plug would then be inserted into the medullar canal to prevent migration of PMMA cement either as the cement was inserted or as the prosthesis was forced into the cement.

Since the shafts of prostheses were conventionally round or of fairly uniform cross-section, it was not difficult to form a plug. However, stems with more elaborate cross-sections, such as the cruciate stem shown in U.S. Pat. No. 5,071,438 have now been proposed and used. Under such circumstances, it is difficult for the surgeon to quickly and accurately prepare a bone plug intraoperatively.

SUMMARY OF OUR INVENTION

We have, therefore, invented an orthopedic bone plug cutter which quickly and simply cuts a customized bone plug for use with stems of complex geometry, such as a cruciate stem. Our bone plug cutter comprises an anvil which supports a piece of bone obtained intraoperatively. A specialized cutting head is provided which is forced against the anvil by a parallel jaw clamp. The cutting head can then be removed from the clamp and the bone plug extruded from the cutter with a plunger.

With the foregoing in mind, it is an object of our invention to provide an orthopedic bone plug cutter which can provide homologous bone plugs of complex geometry.

It is a further object of our invention to provide such a cutter which can be used intraoperatively in a simple manner.

These and other objects and features of our invention will be apparent from the following detailed description taken with reference to the accompanying drawings.

DETAILED DESCRIPTION OF OUR PREFERRED EMBODIMENT

Figure 1:
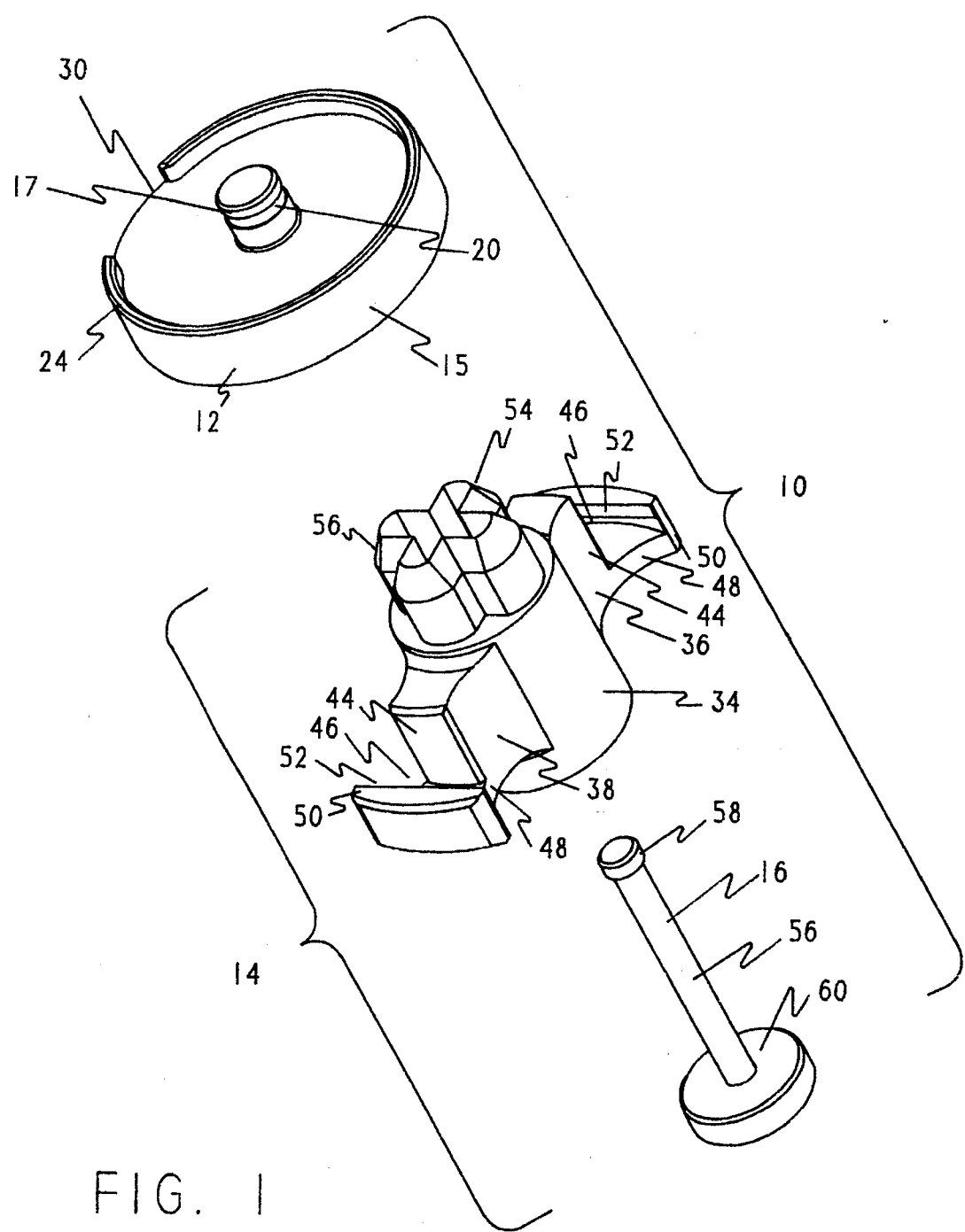
FIG. 1 is a exploded perspective view of the orthopedic bone plug cutter according to our invention.

FIG. 1 illustrates an exploded perspective view of an orthopedic bone plug cutter 10 according to our invention. The cutter 10 comprises an anvil 12 and a cutting head 14. The cutting head 14 has a plunger 16 which is used to remove a bone plug from the cutting head 14.

Figure 2:
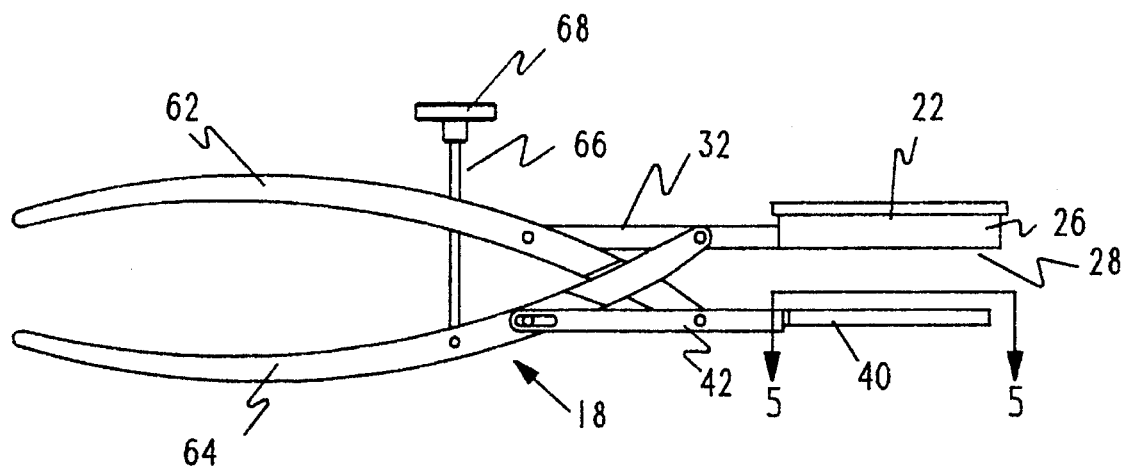
FIG. 2 is a plan view of a parallel jaw clamp for use with our invention.

The anvil 12 comprises a circular plate 15 with a central pin 17 for attaching the anvil 12 to a parallel jaw clamp 18, illustrated in FIG. 2. The pin 16 has a circumferential groove 20 which will receive an o-ring (not shown) so that the pin 16 can be inserted into a bore 22 in the parallel jaw clamp 18. A circumferential rim 24 is also shown on the anvil 12. This rim engages an outer surface 26 on a generally circular jaw 28 in the clamp 18. The rim 24 serves to stabilize the anvil. A gap 30 is also provided in the rim to provide clearance for a parallel arm 32 on the clamp 18.

Figure 5:
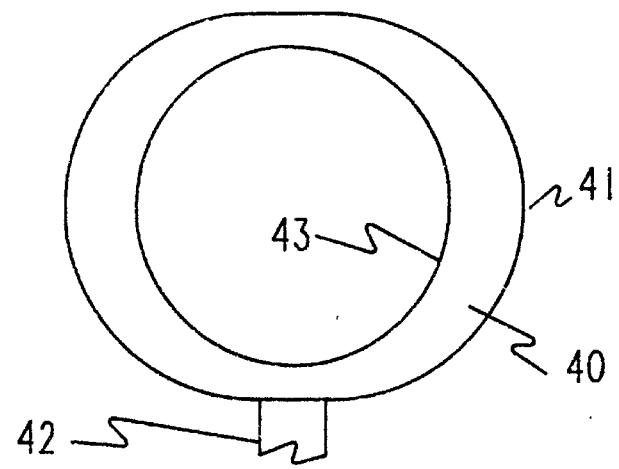
FIG. 5 is a top view of a portion of the clamp of FIG. 2, taken along line 5—5 of FIG. 2.

The cutting head 14 comprises a generally cylindrical body 34 having a through bore for receiving the plunger 16. On opposite sides of the cylindrical body 34 are arms 36, 38 for supporting the cutting head in a ring holder 40 on a second parallel arm 42 on the clamp 18. Each arm 36, 38 comprises a spacer block 44 which will fit tightly on the interior of the ring 40. A slot 46 is formed between the spacer block 44, an extension 48 and a retaining wall 50. The retaining wall 50 fits outside the ring 40. A ridge 52 will engage an upper side of the ring 40. As shown in FIG. 5, the ring 40 has a circular inner surface 43 and a generally elliptical outer surface 41. The cutting head is inserted into the ring and then rotated one-quarter turn to lock the cutting head onto the ring as the ring is progressively captured under the lip 52.

The cutting head 14 has a specialized cutter 54 which confronts the anvil 14. The cutter 54 is shaped to correspond to the perimeter of a distal part of a shaft of the prosthesis being implanted. It can, therefore, assume many different outlines. In the case shown, the outline is cruciate. A bevel 56 is provided on the outside of the specialized cutter 54.

Figure 4:
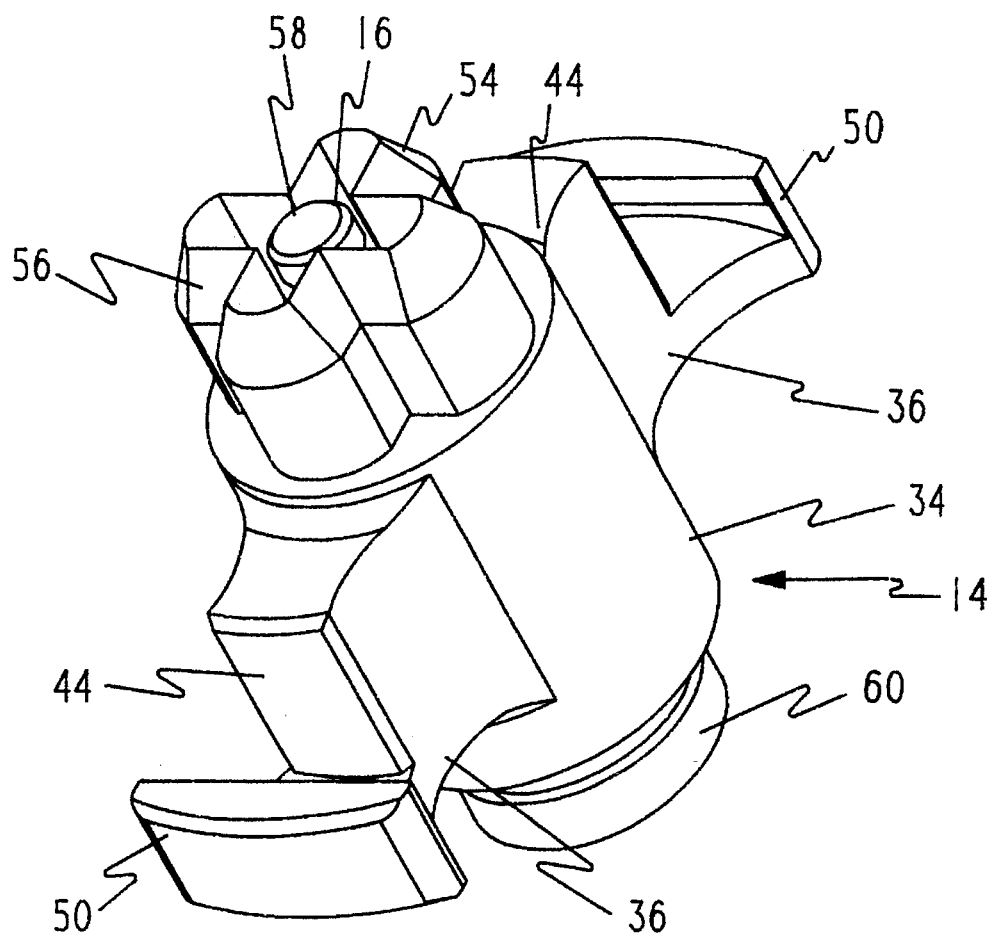
FIG. 4 is a perspective view of a cutting head with plunger according to our invention.

The plunger 16 comprises a shaft 56 with an enlarged end stop 58. At the other end of the shaft 56 there is a handle 60. The handle is preferably screwed on the shaft 56. The bore (not shown) in the cutting head 14 is of a common diameter with the shaft 56, so that when the plunger is assembled, the shaft is first placed in the bore and then the handle 60 is installed, thus capturing the plunger in the cutting head. As shown in FIG. 4, the plunger can be advanced into the specialized cutter 54 to push a bone plug out of the cutter.

The parallel jaw clamp 18 comprises two handles 62, 64 which are pins to the parallel arms 32, 42 as shown in FIG. 2. As threaded rod 66 with a nut 68 allows the parallel jaw clamp to be closed and held with a particular force.

Figure 3:
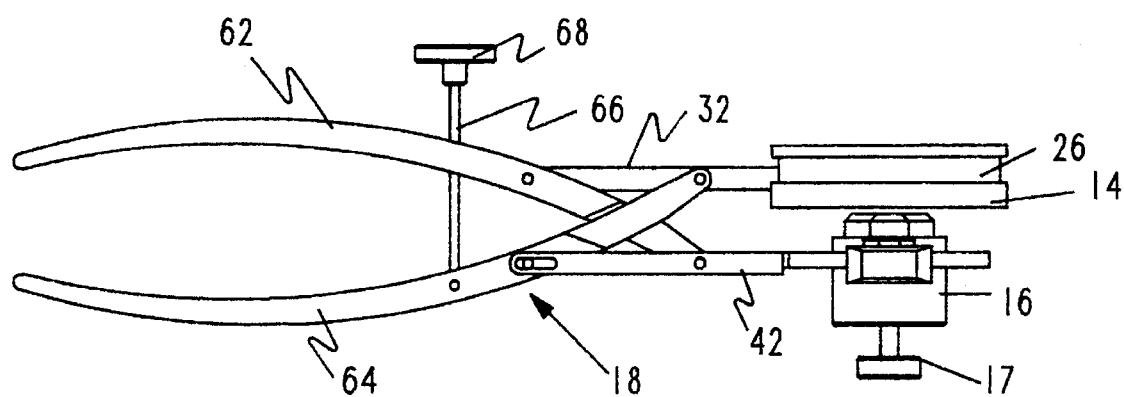
FIG. 3 is a plan view of the orthopedic bone plug cutter of FIG. 1 assembled with the clamp of FIG. 2.

In FIG. 3, the orthopedic bone plug cutter 10 is shown mounted on the parallel jaw clamp 18. To operate the cutter, a piece of bone, obtained intraoperatively, would be placed on the anvil 12 and under the specialized cutter 54. The parallel jaw clamp 18 would then be closed either by manual force on the handles 62, 64 or by tightening the nut 68. When the plug had been successfully cut, the clamp would be released, the cutting head 14 removed from the clamp and the bone plug carefully extruded from the specialized cutter 54 using the plunger 16. The bone plug could then be inserted into a prepared medullary canal in a conventional fashion, prior to implanting the prosthesis with bone cement.

Those skilled in the art will recognize that our invention may be embodied in other specific forms without departing from the spirit or essential teachings thereof. The foregoing description is to be viewed as illustrative and not restrictive. Our invention is defined by the following claims.

We claim as our invention:

1. An orthopedic bone plug cutter for cutting a customized scavenged bone plug for insertion in the medullar canal of a patient to retain bone cement in an area surrounding a prosthesis, said prosthesis having an articulating surface and a shaft adapted to be implanted in the medullar canal, said shaft having a proximal end adapted to be connected to said articulating surface and a distal end spaced away from said articulating surface, said distal end having a perimeter, said bone plug cutter comprising:

means for shaping an intact plug from a segment of bone, said shaping means having a cutting head having a blade on one end thereof, said blade circumscribing a customized perimeter, said customized perimeter being congruent with said perimeter of said distal end of said prosthesis, said blade having an inside wall and an outside wall and a bevel along the perimeter of said outside wall, said bevel extending in an inward and distal direction from said outside wall toward said inside wall;

an anvil confronting said blade; and a clamp means connecting said shaping means and said anvil for forcing said blade of said cutting head against said anvil.

2. The bone plug cutter according to claim 1 wherein said customized perimeter is a cruciate perimeter.

3. The bone plug cutter according to claim 2 further comprising a plunger received within the cutting head for removing said plug from said bone plug cutter.

4. The bone plug cutter according to claim 3 wherein said clamp means further comprise a jaw for supporting said cutting head, said jaw having a generally elliptical outer surface and an inner surface adapted to interface with an outer surface of said head, said head having at least one arm having means for interlocking with said elliptical outer surface of said jaw.

5. The bone plug cutter according to claim 1 wherein said clamp means further comprise a jaw for supporting said cutting head, said jaw having a generally elliptical outer surface and an inner surface adapted to interface with an outer surface of said head, said head having at least one arm having means for interlocking with said elliptical outer surface of said jaw.

6. The bone plug cutter according to claim 1 wherein said clamp means comprise a parallel jaw clamp having at least two jaws for forcing said blade against said anvil and means for maintaining said jaws in parallel relationship to each other as said blade is forced against said anvil.

7. The bone plug cutter according to claim 6 wherein said clamp means further comprise a jaw for supporting said cutting head, said jaw having a generally elliptical outer surface and an inner surface adapted to interface with an outer surface of said head, said head having at least one arm having means for interlocking with said elliptical outer surface of said jaw.

8. The bone plug cutter according to claim 1 further comprising a plunger received within the cutting head for removing said plug from said bone plug cutter.

9. The bone plug cutter according to claim 8 wherein said clamp means further comprise a jaw for supporting said cutting head, said jaw having a generally elliptical outer surface and an inner surface adapted to interface with an outer surface of said head, said head having at least one arm having means for interlocking with said elliptical outer surface of said jaw.

* * * * *